US005714383A

United States Patent [19]
Thompson

[11] Patent Number: 5,714,383
[45] Date of Patent: Feb. 3, 1998

[54] METHOD AND REAGENT FOR TREATING CHRONIC MYELOGENOUS LEUKEMIA

[75] Inventor: James D. Thompson, Boulder, Colo.

[73] Assignee: Ribozyme Pharmaceuticals, Inc., Boulder, Colo.

[21] Appl. No.: 363,233

[22] Filed: Dec. 23, 1994

Related U.S. Application Data

[63] Continuation-in-part of Ser. No. 193,922, Feb. 7, 1994, abandoned, which is a continuation of Ser. No. 882,822, May 14, 1992.

[51] Int. Cl.$^6$ ............................ C12N 15/11; C12N 15/85
[52] U.S. Cl. .................... 435/366; 435/320.1; 536/23.1; 514/44
[58] Field of Search ........................... 514/44; 536/23.1; 435/240.2, 320.1, 366

[56] References Cited

U.S. PATENT DOCUMENTS 4,987,071 1/1991 Cech et al. .............................. 435/91

FOREIGN PATENT DOCUMENTS 9118913 12/1991 WIPO.

OTHER PUBLICATIONS

Ballantyne et al., "Nucleotide sequence of the cDNA for murine intercellular adhesion molecule-1 (ICAM-1)," *Nucleic Acids Research* 17:5853 (1989).

Barinaga, "Ribozymes: Killing the Messenger," *Science* 262:1512–1514 (1993).

Cotten, "The in vivo application of ribozymes," *TIBTECH* 8:174–178 (1990).

Edgington, "Ribozymes: Stop Making Sense," *Biotechnology* 10:256–262 (1992).

Kita et al., "Sequence and expression of rat ICAM-1," *Biochem. Biophys. Acta* 1131:108–110 (1992).

Simons et al., "ICAM, an adhesion ligand of LFA-1, is homologous to the neural cell adhesion molecule NCAM," *Nature* 331:624–627 (1988).

Apperley et al., *Br. J. Haematol* 69:239 (1988).

Carter, "Adeno-Associated Virus Vectors," *Curr Opi. Biotech.* 3:533–539 (1992).

Cech, "Ribozymes and Their Medical Implications," *JAMA* 260:3030–3034 (1988).

Chen et al., "Multitarget-Ribozyme Directed to Cleave at up to Nine Highly Conserved HIV-1 env RNA Regions Inhibits HIV-1 Replication–Potential Effectiveness Against Most PresentlySequenced HiV-1 Isolates," *Nucleic Acids Research* 20:4581–4589 (1992).

Chowrira and Burke, "Extensive Phosphorothioate Substitution Yields Highly Active and Nuclease-Resistant Hairpin Ribozymes," *Nucleic Acids Res.* 20:2835–2840 (1992).

Chowrira et al., "In Vitro and in Vivo Comparison of Hammerhead, Hairpin, and Hepatitis Delta Virus Self-Processing Ribozymes Cassettes," *J. Biol. Chem.* 269:25856–25864 (1994).

Collins and Olive, "Reaction Conditions and Kinetics of Self-Cleavage of a Ribozyme Derived From Neurospora VS RNA," *Biochemistry* 32:2795–2799 (1993).

Daley et al., *Science* 247:842 (1990).

Dropulic et al., "Functional Characterization of a U5 Ribozyme: Intracellular Suppression of Human Immunodeficiency Virus Type I Expression," *Journal of Virology* 66:1432–1441 (1992).

Elroy-Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Gao and Huang, "Cytoplasmic Expression of a Reporter Gene by Co-Delivery of T7 RNA Polymerase and T7 Promoter Sequence with Cationic Liposomes," *Nucleic Acids Res.* 21:2867–2872 (1993).

Guerrier-Takada et al., "The RNA Moiety of Ribonuclease P Is the Catalytic Subunit of the Enzyme," *Cell* 35:849–857 (1983).

Hampel and Tritz, "RNA Catalytic Properties of the Minimum (-)sTRSV Sequence," *Biochemistry* 28:4929–4933 (1989).

Hampel et al., "'Hairpin' Catalytic RNA Model: Evidence for Helices and Sequence Requirement for Substrate RNA," *Nucleic Acids Research* 18:299–304 (1990).

Haseloff and Gerlach, "Simple RNA Enzymes with New and Highly Specific Endoribonuclease Activities," *Nature* 334:585–591 (1988).

Heisterkamp et al., *Nature* 315:758 (1985).

Heisterkamp, *Nature* 344:251 (1990).

Heisterkamp, *Nucleic Acids Research* 16:10069 (1988).

Hertel et al., "Numbering System for the Hammerhead," *Nucleic Acids Res.* 20:3252 (1992).

Hooberman et al., *Proc. Natl. Acad. Sci. USA* 86:4259 (1989).

Jaeger et al., "Improved Predictions of Secondary Structures for RNA," *Proc. Natl. Acad. Sci. USA* 86:7706–7710 (1989).

Jeffries and Symons, "A Catalytic 13-mer Ribozyme," *Nucleic Acids Research* 17:1371–1377 (1989).

Kashani-Sabet et al., "Reversal of the Malignant Phenotype by an Anti-ras Ribozyme," *Antisense Research & Development* 2:3–15 (1992).

Kim and Cech, "Three-dimensional model of the active site of the self-splicing rRNA precursor of Tetrahymena," *Proc. Natl. Acad. Sci. USA* 84:8788 (1987).

L'Huillier et al., "Cytoplasmic Delivery of Ribozymes Leads to Efficient Reduction in α-Lactalbumin mRNA Levels in C1271 Mouse," *Embo J.* 11:4411–4418 (1992).

Lieber et al., "Stable High-Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

(List continued on next page.)

Primary Examiner—Charles L. Patterson, Jr.
Attorney, Agent, or Firm—Lyon & Lyon LLP

[57] ABSTRACT

An enzymatic RNA molecule which cleaves mRNA associated with development or maintenance of CML.

26 Claims, 6 Drawing Sheets

OTHER PUBLICATIONS

Milligan and Uhlenbeck, "Synthesis of Small RNAs Using T7 RNA Polymerase," *Methods Enzymol.* 180:51–62 (1989).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Rossi et al, "Ribozymes as Anti–HIV–1 Therapeutic Agents: Principles, Applications, and Problems," *Aids Research and Human Retroviruses* 8:183–189 (1992).

Sarver et al., "Catalytic RNAs (Ribozymes): A New Frontier in Biomedical Applications," *AIDS Res. Rev.* 2:259 (1992).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Shtivelman et al., *Blood* 69:971 (1987).

Szcylik et al., *Science* 253:562 (1991)

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Uhlenbeck, "A Small Catalytic Oligoribonucleotide," *Nature* 328:596–600 (1987).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme," *Journal of Virology* 65:5531–5534 (1994).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Functional mRNA in Mammalian Cells by Bacteriophage T3 RNA Polymerase," *Mol. Cell. Biol.* 10:4529–4537 (1990).

Usman and Cedergren, "Exploiting the chemical synthesis of RNA," *TIBS* 17:334–339 (1992).

TARGET RNA
+DNA OLIGO
+RNAse H

METHOD AND REAGENT FOR TREATING CHRONIC MYELOGENOUS LEUKEMIA

This application is a Continuation-In-Part of Thompson "Method and Reagent for Treating Chronic Myelogenous Leukemia", U.S. Ser. No. 08/193,922 (filed on Feb. 7, 1994), now abandoned, which is a FWC of U.S. Ser. No. 07/882,822 (filed on May 14, 1992), and hereby incorporated by reference herein (including drawings).

BACKGROUND OF THE INVENTION

The following is a description of relevant art, none of which is admitted to be prior art to the pending claims.

This invention relates to methods for inhibition of growth of transformed cells, and inhibition of progression to a transformed phenotype in pre-neoplastic cells.

Transformation is a cumulative process whereby normal control of cell growth and differentiation is interrupted, usually through the accumulation of mutations affecting the expression of genes that regulate cell growth and differentiation.

Chronic myelogenous leukemia (CML) exhibits a characteristic disease course, presenting initially as a chronic granulocytic hyperplasia, and invariably evolving into an acute leukemia which is caused by the clonal expansion of a cell with a less differentiated phenotype (i.e., the blast crisis stage of the disease). CML is an unstable disease which ultimately progresses to a terminal stage which resembles acute leukemia. This lethal disease affects approximately 16,000 patients a year. Chemotherapeutic agents such as hydroxyurea or busulfan can reduce the leukemic burden but do not impact the life expectancy of the patient (e.g. approximately 4 years). Consequently, CML patients are candidates for bone marrow transplantation (BMT) therapy. However, for those patients which survive BMT, disease recurrence remains a major obstacle (Apperley et al., 1988 *Br. J. Haematol.* 69, 239).

The Philadelphia (Ph) chromosome which results from the translocation of the abl oncogene from chromosome 9 to the bcr gene on chromosome 22 is found in greater than 95% of CML patients and in 10–25% of all cases of acute lymphoblastic leukemia [(ALL); Fourth International Workshop on Chromosomes in Leukemia 1982, *Cancer Genet. Cytogenet.* 11,316]. In virtually all Ph-positive CMLs and approximately 50% of the Ph-positive ALLs, the leukemic cells express bcr-abl fusion mRNAs in which exon 2 (b2-a2 junction) or exon 3 (b3-a2 junction) from the major breakpoint cluster region of the bcr gene is spliced to exon 2 of the abl gene. Heisterkamp et al., 1985 *Nature* 315, 758; Shtivelman et al., 1987, *Blood* 69, 971). In the remaining cases of Ph-positive ALL, the first exon of the bcr gene is spliced to exon 2 of the abl gene (Hooberman et al., 1989 *Proc. Nat. Acad. Sci. USA* 86, 4259; Heisterkamp et al., 1988 *Nucleic Acids Res.* 16, 10069).

The b3-a2 and b2-a2 fusion mRNAs encode 210 kd bcr-abl fusion proteins which exhibit oncogenic activity (Daley et al., 1990 *Science* 247, 824; Heisterkamp et al., 1990 *Nature* 344, 251). The importance of the bcr-abl fusion protein (p210$^{bcr-abl}$) in the evolution and maintenance of the leukemic phenotype in human disease has been demonstrated using antisense oligonucleotide inhibition of p210$^{bcr-abl}$ expression. These inhibitory molecules have been shown to inhibit the in vitro proliferation of leukemic cells in bone marrow from CML patients. Szczylik et al., 1991 *Science* 253, 562).

Reddy, U.S. Pat. No. 5,246,921 (hereby incorporated by reference herein) describes use of ribozymes as therapeutic agents for leukemias, such as chronic myelogenous leukemia (CML) by targeting the specific junction region of bcr-abl fusion transcripts. It indicates causing cleavage by a ribozyme at or near the breakpoint of such a hybrid chromosome, specifically it includes cleavage at the sequence GUX, where X is A, U or G. The one example presented is to cleave the sequence 5' AGC AG AGUU (cleavage site) CAA AAGCCCU-3'(SEQ ID NO. 32).

Scanlon WO 91/18625, WO 91/18624, and WO 91/18913 describes a ribozyme effective to cleave oncogenic variants of H-ras RNA. This ribozyme is said to inhibit H-ras expression in response to external stimuli.

SUMMARY OF THE INVENTION

The invention features use of ribozymes to inhibit the development or expression of a transformed phenotype in man and other animals by modulating expression of a gene that contributes to the expression of CML. Cleavage of targeted mRNAs expressed in pre-neoplastic and transformed cells elicits inhibition of the transformed state.

Ribozymes are RNA molecules (which term includes molecules which may have modified sugar, base or phosphate-containing groups compared to a ribonucleotide, see below; that is, the term RNA encompasses any nucleic acid containing at least one ribonucleotide, and which may contain moieties other than nucleotides) having an enzymatic activity which is able to repeatedly cleave other separate RNA molecules in a nucleotide base sequence specific manner. Such enzymatic RNA molecules can be targeted to virtually any RNA transcript and efficient cleavage has been achieved in vitro (Kim et al., 1987 *Proc. Nat. Acad. of Sci. USA* 84, 8788; Haseloff and Gerlach, 1988 *Nature* 334, 585; Cech, 1988 *JAMA* 260, 3030 and Jefferies et al., 1989 *Nucleic Acid Research* 17, 1371).

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

By the phrase "enzymatic RNA molecule" is meant an RNA molecule which has complementarity in a substrate binding region to a specified gene target, and also has an enzymatic activity which is active to specifically cleave RNA in that target. That is, the enzymatic RNA molecule is able to intramolecularly or intermolecularly cleave RNA and thereby inactivate a target RNA molecule. This complementarity functions to allow sufficient hybridization of the enzymatic RNA molecule to the target RNA to allow the cleavage to occur. 100% complementarity is preferred, but complementarity as low as 50-75% may also be useful in this invention. This class of chemicals exhibits a high degree of specificity for cleavage of the intended target mRNA. Consequently, the ribozyme agent will only affect cells expressing that particular gene, and will not be toxic to other tissues.

The invention can be used to treat cancer or pre-neoplastic conditions. Two preferred administration protocols can be used, either in vivo administration to reduce the tumor burden, or ex vivo treatment to eradicate transformed cells from tissues such as bone marrow prior to reimplantation.

Thus, in the first aspect the invention features an enzymatic RNA molecule (or ribozyme) which cleaves mRNA associated with development or maintenance of CML. Those mRNAs are the mRNA targets sites disclosed in Table II (standard reference numbers for the sites are provided for reference). These targets are present in the 425 nucleotides surrounding the fusion sites of the bcr and abl sequences in the b2-a2 and b3-a2 recombinant mRNAs. Other sequences in the 5' portion of the bcr mRNA or the 3' portion of the abl mRNA may also be targeted for ribozyme cleavage. Cleavage at any of these sites in the fusion mRNA molecules will result in inhibition of translation of the fusion protein in treated cells.

In preferred embodiments of this invention, the enzymatic nucleic acid molecule is formed in a hammerhead (HH) or hairpin motif or hepatitis delta virus, but may also be formed in the motif of a group I intron or RNaseP RNA (in association with an RNA guide sequence) or Neurospora VS RNA. Examples of such hammerhead motifs are described by Rossi et al., 1992. *Aids Research and Human Retroviruses*, 8, 183, of hairpin motifs by Hampel et al., "RNA Catalyst for Cleaving Specific RNA Sequences," European 0360257 Hampel and Tritz, 1989, *Biochemistry*, 28, 4929, and Hampel et al., 1990, *Nucleic Acids Res.* 18, 299; an example of the hepatitis delta virus motif is described by Perrotta and Been, 1992, *Biochemistry*, 31, 16, of the RNaseP motif by Guerrier-Takada et al., 1983, *Cell*, 35, 849, Neurospora VS RNA ribozyme motif is described by Collins (Saville and Collins, 1990 *Cell* 61, 685; Saville and Collins, 1991 *Proc. Natl. Acad. Sci. USA* 88, 8826; Collins and Olive, 1993 *Biochemistry* 32, 2795) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

By "complementarity" is meant a nucleic acid that can form hydrogen bond(s) with other RNA sequence by either traditional Watson-Crick or other non-traditional types (for example Hoogsteen type) of base-paired interactions.

In other aspects, the invention features: (a) a mammalian cell which includes an enzymatic RNA molecule as described above (preferably, the mammalian cell is a human cell ); (b) an expression vector which includes nucleic acid encoding an enzymatic RNA molecule described above, located in the vector, e.g., in a manner which allows expression of that enzymatic RNA molecule within a mammalian cell; (c) a method for treatment of CML by administering to a patient an enzymatic RNA molecule as described above; and (d) a method for treatment of CML by ex vivo treatment of blood or marrow cells with an enzymatic RNA molecule as described above.

The invention provides a class of chemical cleaving agents which exhibit a high degree of specificity for the mRNA causative of CML. Such enzymatic RNA molecules can be delivered exogenously or endogenously to afflicted cells. In the preferred hammerhead motif the small size (less than 40 nucleotides, preferably between 32 and 36 nucleotides in length) of the molecule allows the cost of treatment to be reduced.

The smallest ribozyme delivered for any type of treatment reported to date (by Rossi et al., 1992 supra) is an in vitro transcript having a length of 142 nucleotides. Synthesis of ribozymes greater than 100 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, an alternative approach uses smaller ribozyme motifs (e.g., of the hammerhead structure, shown generally in FIG. 1) and exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure, as well as complementary binding of the ribozyme to the mRNA target.

The enzymatic RNA molecules of this invention can be used to treat human CML or precancerous conditions. Affected animals can be treated at the time of cancer detection or in a prophylactic manner. This timing of treatment will reduce the number of affected cells and disable cellular replication. This is possible because the ribozymes are designed to disable those structures required for successful cellular proliferation.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al, 1992 *Proc. Natl. Acad. Sci. USA* 89, 10802–6; Chen et al., 1992 *Nucleic Acids Res.,* 20, 4581–9; Sarver et al, 1990 *Science* 247, 1222–1225). Those skilled in the art realize that any ribozyme can be expressed in eukaryotic cells from the appropriate DNA/RNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992 *Nucleic Acids Symp. Ser,* 27, 15–6; Taira et al., 1991, *Nucleic Acids Res.,* 19, 5125–30; Ventura et al., 1993 *Nucleic Acids Res.,* 21, 3249–55; Chowrira et al., 1994 *J. Biol. Chem.* 269, 25856).

Such ribozymes are useful for the prevention of the diseases and conditions discussed above, and any other diseases or conditions that are related to the level of $p210^{bcr-abl}$ activity in a cell or tissue. By "related" is meant that the inhibition of $p210^{bcr-abl}$ mRNAs and thus reduction in the level of protein activity will relieve to some extent the symptoms of the disease or condition.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II and III. Examples of such ribozymes are shown in Tables IV. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit $p210^{bcr-abl}$ activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

The invention features ribozymes that inhibit $p210^{bcr-abl}$ production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target $p210^{bcr-abl}$ encoding mRNAs, preventing translation and protein accumulation. In the absence of the expression of the target gene, a therapeutic effect may be observed.

By "inhibit" is meant that the activity or level of $p210^{bcr-abl}$ encoding mRNA is reduced below that observed in the absence of the ribozyme, and preferably is below that level observed in the presence of an enzymatically inactive RNA molecule able to bind to the same site on the mRNA, but unable to cleave that RNA.

Such ribozymes are useful for the prevention of the diseases and conditions discussed above, and any other diseases or conditions that are related to the level of $p210^{bcr-abl}$ activity in a cell or tissue. By "related" is meant that the inhibition of bcr-abl mRNA translation, and thus reduction in the level of $p210^{bcr-abl}$, will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues through the use of a catheter, infusion pump or stent, with or without their incorporation in biopolymers. In preferred embodiments, the ribozymes have binding arms which are complementary to the sequences in Tables II and III. Examples of such ribozymes are shown in Table IV.

Examples of such ribozymes consist essentially of sequences defined in this Table. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit $p210^{bcr-abl}$ activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawing will first briefly be described.

Drawing

FIG. 1 is a diagrammatic representation of a hammerhead motif ribozyme (SEQ ID NO. 35) showing stems I, II and III interacting with a target region. The 5' and 3' ends of both ribozyme and target are shown. Stem II can be ≧2 base-pair long.

FIG. 2a is a diagrammatic representation of the hammerhead ribozyme domain known in the art; FIG. 2b is a diagrammatic representation of the hammerhead ribozyme as divided by Uhlenbeck (1987, *Nature,* 327, 596–600) into a substrate and enzyme portion; FIG. 2c is a similar diagram showing the hammerhead divided by Haseloff and Gerlach (1988, *Nature*, 334, 585-591) into two portions; and FIG. 2d is a similar diagram showing the hammerhead divided by Jeffries and Symons (1989, *Nucl. Acids. Res.*, 17, 1371-1371 ) into two portions.

FIG. 3 is a diagrammatic representation of the general structure of a hairpin ribozyme (SEQ ID NO. 37) and substrate RNA (SEQ ID NO. 36). Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H, refers to bases A, U or C. Y refers to pyrimidine bases."

Figure 6:
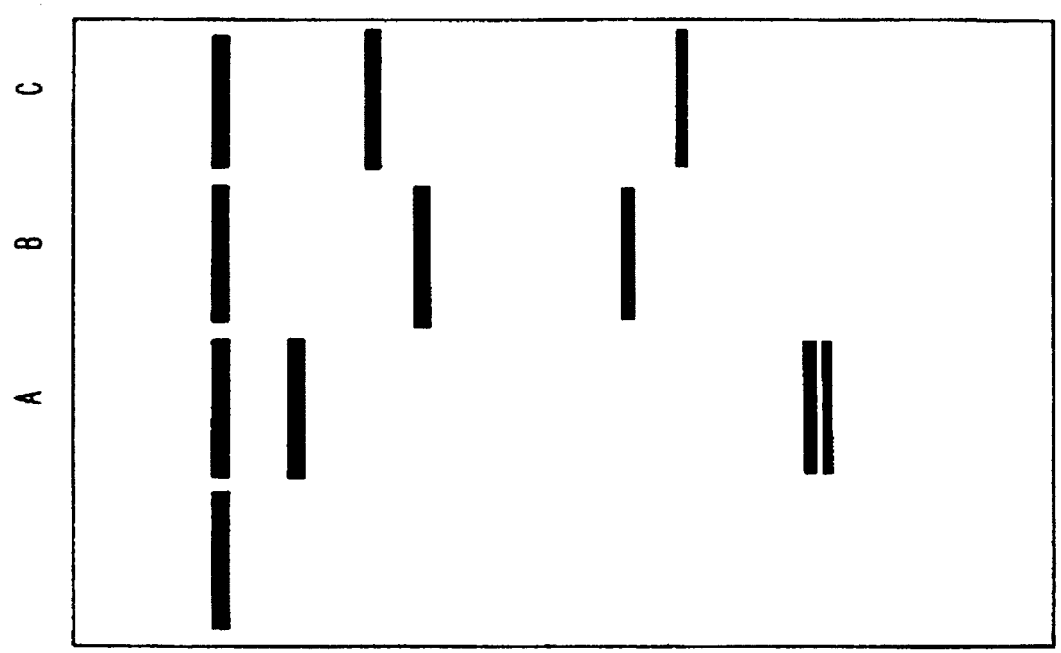
Figure 6:
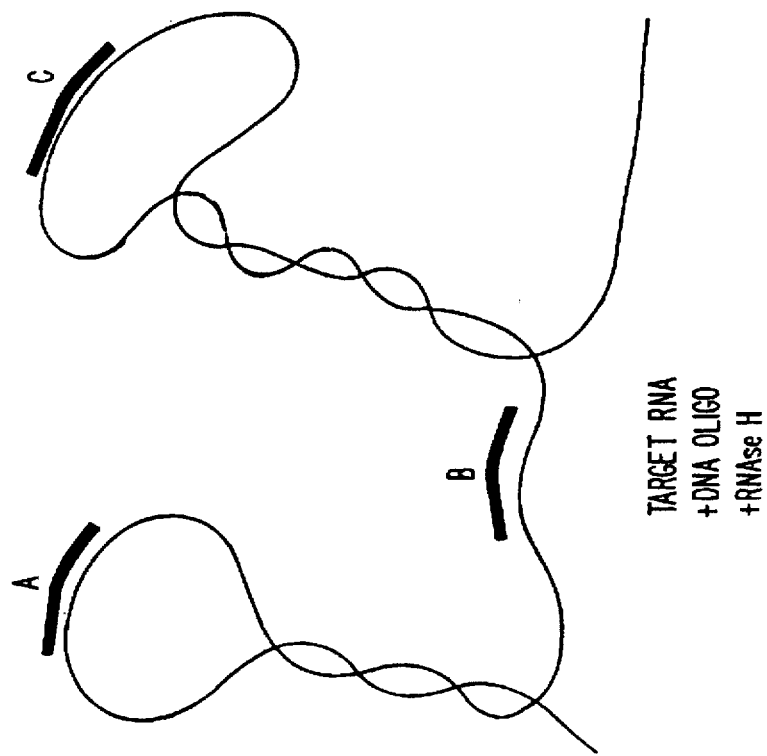

FIG. 6 is a schematic representation of an RNase H accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Ribozymes

Ribozymes of this invention block to some extent p210$^{bcr-abl}$ expression and can be used to treat disease or diagnose such disease. Ribozymes will be delivered to cells in culture and to tissues in animal models of CML. Ribozyme cleavage of bcr/abl mRNA in these systems may prevent or alleviate disease symptoms or conditions.

Target sites

Targets for useful ribozymes can be determined as disclosed in Draper et al supra, Sullivan et al., supra., as well as by Draper et al., "Method and reagent for treatment of arthritic conditions" U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein.

The sequence of human bcr/abl mRNA can be screened for accessible sites using a computer folding algorithm. Regions of the mRNA that did not form secondary folding structures and that contain potential hammerhead or hairpin ribozyme cleavage sites can be identified. These sites are shown in Tables II and III (All sequences are 5' to 3' in the tables). The nucleotide base position is noted in the Tables as that site to be cleaved by the designated type of ribozyme.

It must be established that the sites predicted by the computer-based RNA folding algorithm correspond to potential cleavage sites. Hammerhead ribozymes are designed that could bind and are individually analyzed by computer folding (Jaeger et al., 1989 *Proc. Natl. Acad. Sci. USA*, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application 07/883,849 filed May 1, 1992, entitled "Assay for ribozyme target site," hereby incorporated by reference herein. Briefly, DNA oligonucleotides representing potential hammerhead or hairpin ribozyme cleavage sites are synthesized. A polymerase chain reaction is used to generate a substrate for T7 RNA polymerase transcription from human bcr/abl cDNA clones. Labeled RNA transcripts are synthesized in vitro from the two templates. The oligonucleotides and the labeled transcripts are annealed, RNaseH is added and the mixtures are incubated for the designated times at 37° C. Reactions are stopped and RNA separated on sequencing polyacrylamide gels. The percentage of the substrate cleaved is determined by autoradiographic quantitation using a phosphor imaging system. From these data, hammerhead ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 *J. Am. Chem. Soc.*, 109, 7845 and in Scaringe et al., 1990 *Nucleic Acids Res.*, 18, 5433 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for G₅ and a U for A₁₄ (numbering from Hertel et al., 1992 *Nucleic Acids Res.*, 20, 3252). Hairpin ribozymes are synthesized in two parts and annealed to reconstruct the active ribozyme (Chowrira and Burke, 1992 *Nucleic Acids Res.*, 20, 2835–2840). Ribozymes are also synthesized from DNA templates using bacteriophage T7 RNA polymerase (Milligan and Uhlenbeck, 1989, *Methods Enzymol.* 180, 51). All ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34). Ribozymes are purified by gel electrophoresis using general methods or are purified by high pressure liquid chromatography (HPLC; See Usman et al. Synthesis, deprotection, analysis and purification of RNA and ribozymes, filed May 18, 1994, U.S. Ser. No. 08/245,736 the totality of which is hereby incorporated herein by reference) and are resuspended in water.

The sequences of the chemically synthesized ribozymes most useful in this study are shown in Table IV. Those in the art will recognize that these sequences are representative only of many more such sequences where the enzymatic portion of the ribozyme (all but the binding arms) is altered to affect activity. For example, stem-loop II sequence of hammerhead ribozymes listed in Table IV (5'-GGCCGAAAGGCC-3') (SEQ ID NO. 33) can be altered (substitution, deletion, and/or insertion) to contain any sequence provided, a minimum of two base-paired stem structure can form. The sequences listed in Tables IV may be formed of ribonucleotides or other nucleotides or non-nucleotides. Such ribozymes are equivalent to the ribozymes described specifically in the Tables.

Optimizing Ribozyme Activity

Figure 2B:
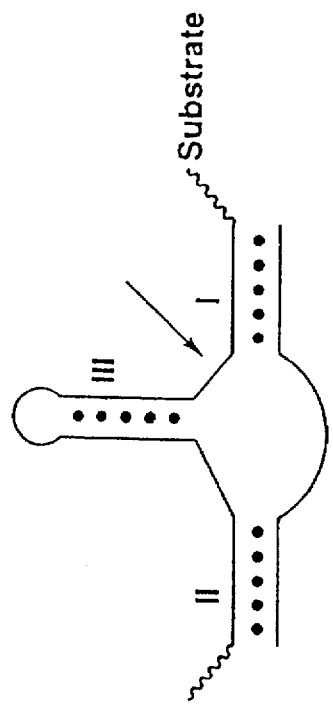
Figure 2D:
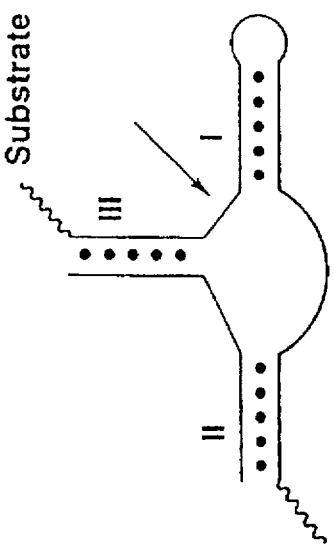
Figure 2A:
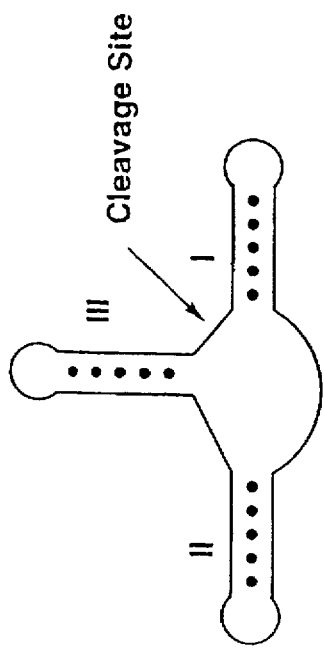
Figure 2C:
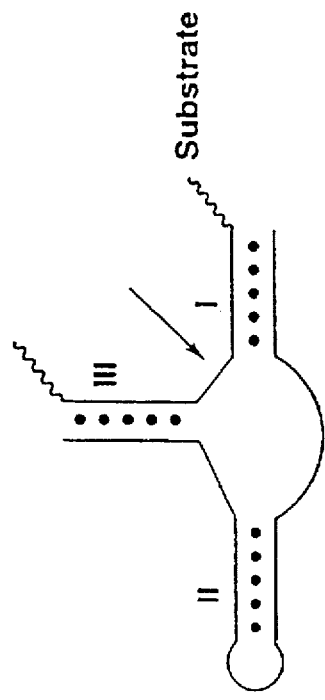

Ribozyme activity can be optimized as described by Stinchcomb et al. supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application 07/829,729, and Sproat, European Patent Application 92110298.4 which describe various chemical modifications that can be made to the sugar moieties of enzymatic RNA molecules and/or modifications which enhance their efficacy in cells, and removal of stem II bases to shorten RNA synthesis times and reduce chemical requirements. (All these publications are hereby incorporated by reference herein.).

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci, USA,* 87, 6743–7; Gao and Huang 1993 *Nucleic Acids Res.,* 21, 2867–72; Lieher et al., 1993 *Methods Enzymol.,* 217, 47–66; Zhou et al., 1990 *Mol. Cell. Biol.,* 10, 4529–37). Several investigators have demonstrated that ribozymes expressed from such promoters can function in mammalian cells (e.g. Kashani-Sabet et al., 1992 *Antisense Res. Dev.,* 2, 3–15; Ojwang et al., 1992 *Proc. Natl. Acad. Sci. USA,* 89, 10802–6; Chen et al., 1992 *Nucleic Acids Res.,* 20, 4581–9; Yu et al., 1993 *Proc. Natl. Acad. Sci. USA,* 90, 6340–4; L'Huillier et al., 1992 *EMBO J.* 11, 4411–8; Lisziewicz et al., 1993 *Proc. Natl. Acad. Sci. U.S.A.,* 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves mRNAs encoded by bcr-abl is inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo.

In another preferred embodiments, the ribozyme is administered to the site of bcr-abl expression in an appropriate liposomal vesicle.

EXAMPLE 1 bcr-abl Hammerhead ribozymes

By engineering ribozyme motifs we have designed several ribozymes directed against bcr-abl mRNA sequences.

These have been synthesized with modifications that improve their nuclease resistance. These ribozymes cleave bcr-abl target sequences in vitro.

The ribozymes are tested for function in vivo by exogenous delivery to cells expressing bcr-abl. Ribozymes are delivered by incorporation into liposomes, by complexing with cationic lipids, by microinjection, or by expression from DNA vectors. Expression of bcr-abl is monitored by ELISA, by indirect immunofluoresence, and/or by FACS analysis. Levels of bcr-abl mRNA are assessed by Northern analysis, RNase protection, by primer extension analysis or by quantitative RT-PCR techniques. Ribozymes that block the induction of $p210^{bcr-abl}$ protein and mRNA by more than 20% are identified.

Diagnostic uses

Ribozymes of this invention may be used as diagnostic tools to examine genetic drift and mutations within diseased cells. They are also useful to detect the presence of bcr-abl fusions in the presence of bcr or abl mRNAs. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with a cancer related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., $p210^{bcr-abl}$)) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.

RNASeP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Figure 1:
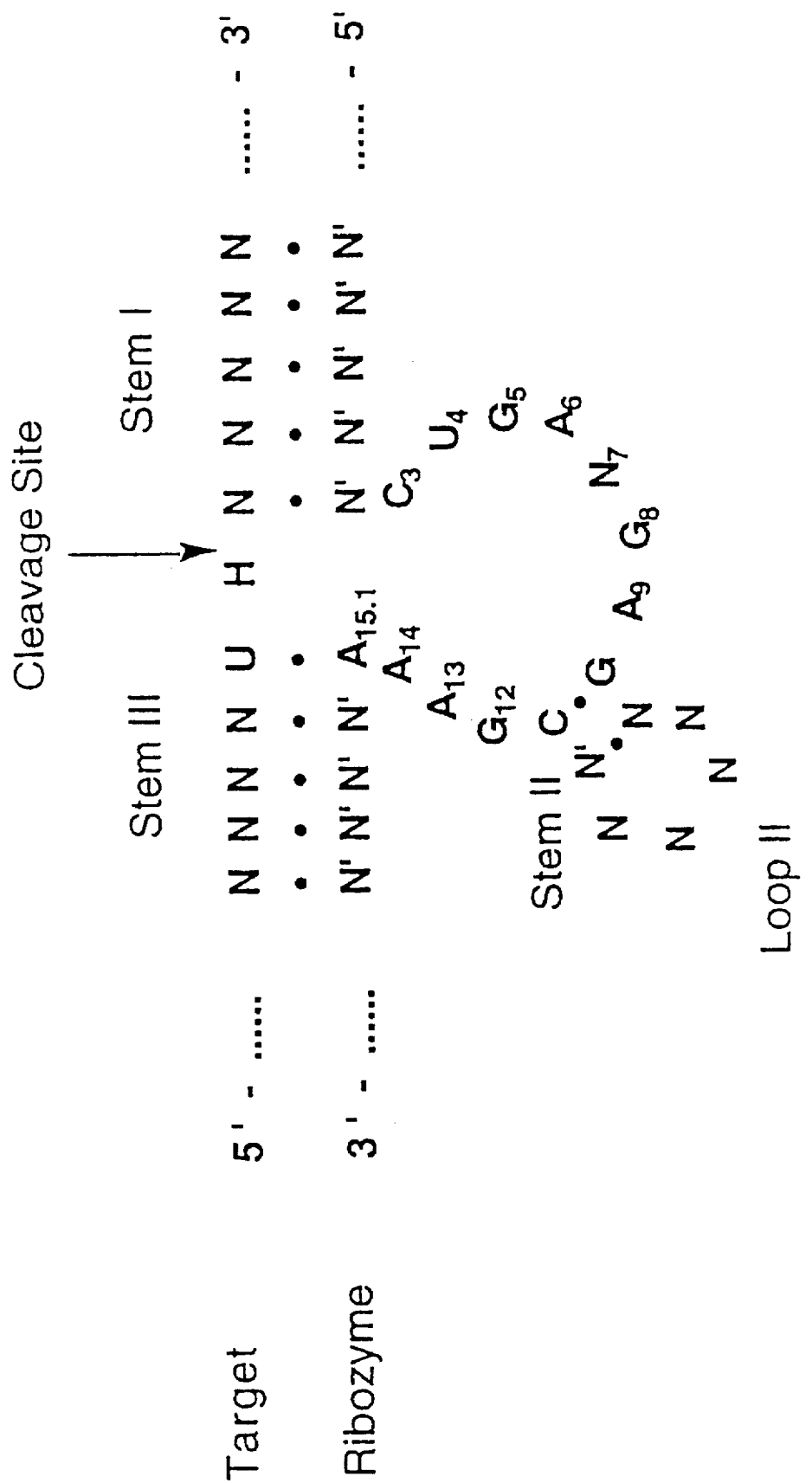

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIGS. 1 and 2)

Hairpin Ribozyme

Figure 3:
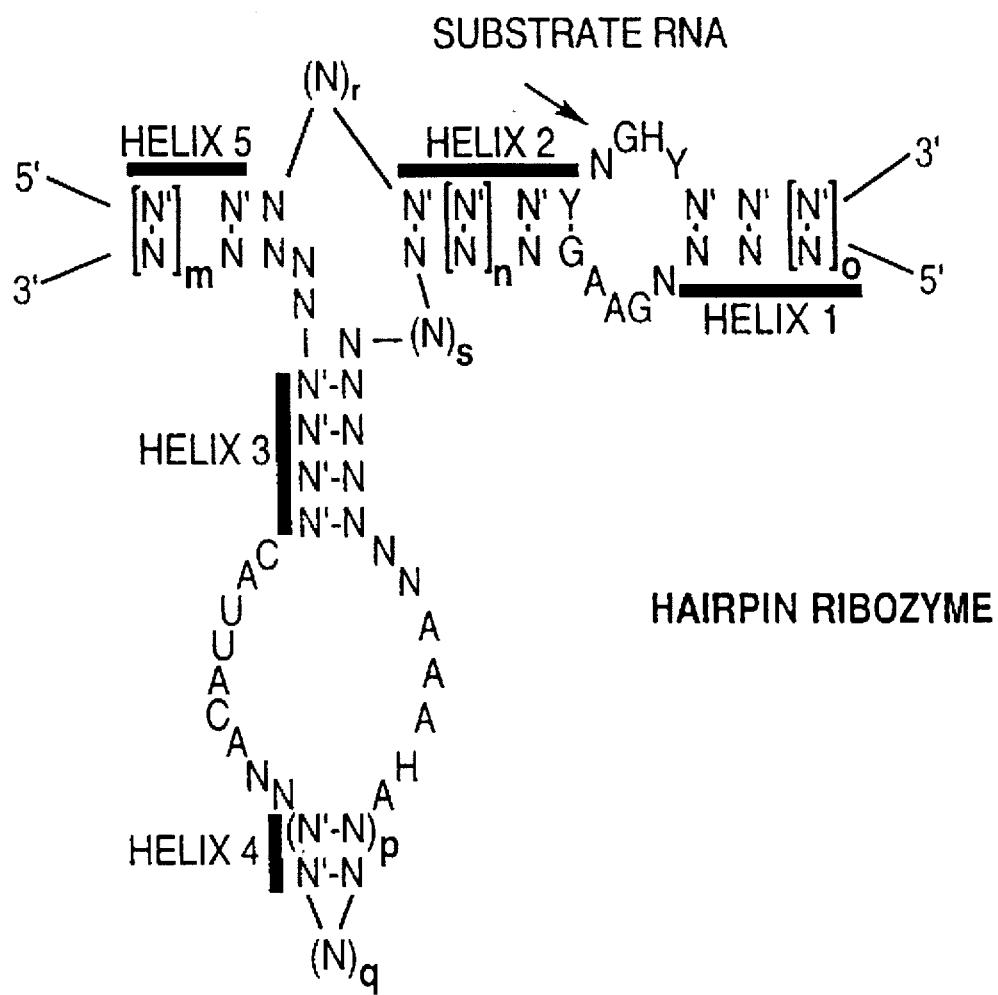

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Figure 4:
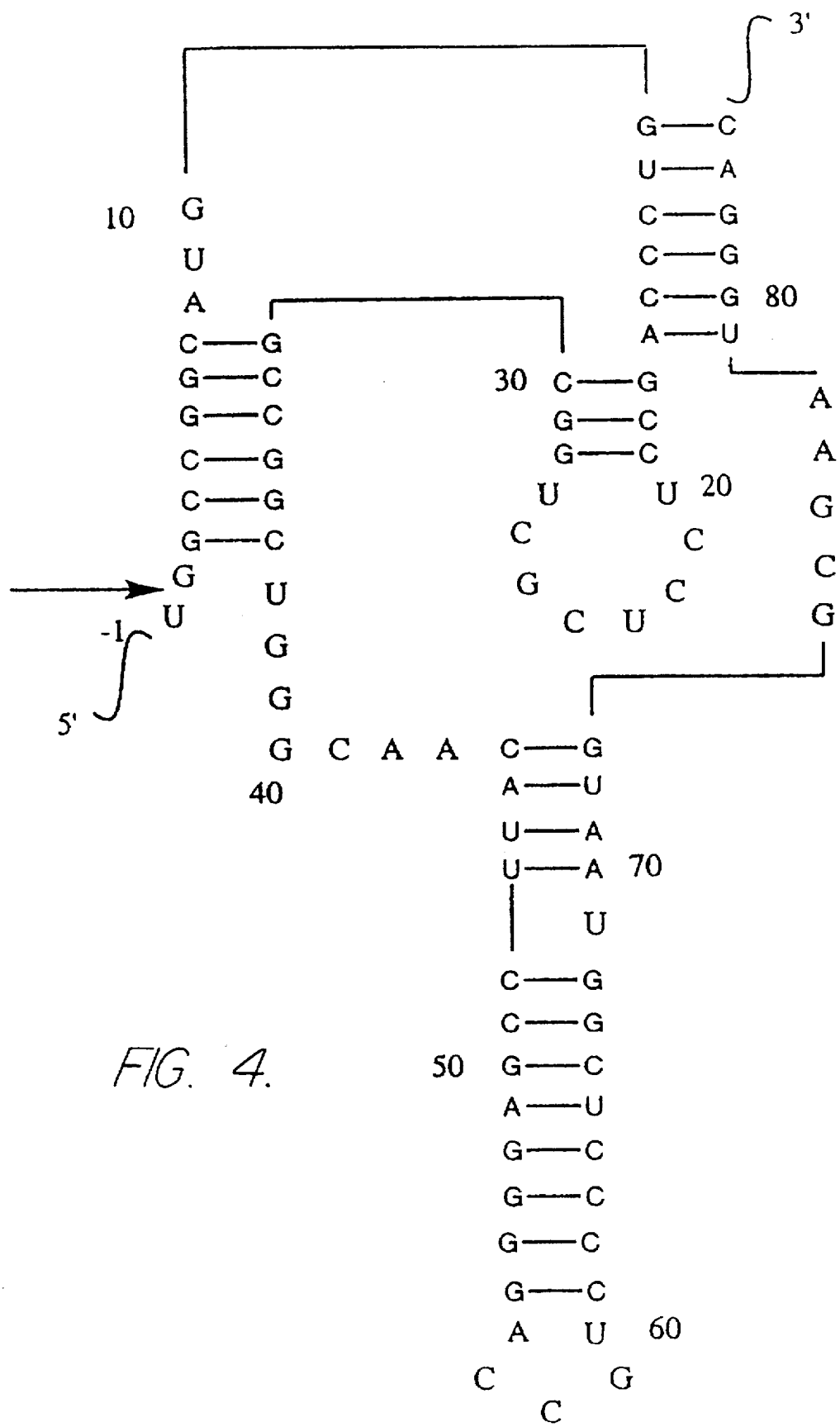
FIG. 4 is a representation of the general structure of the hepatitis delta virus ribozyme domain (SEQ ID NO. 38) known in the art.

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Figure 5:
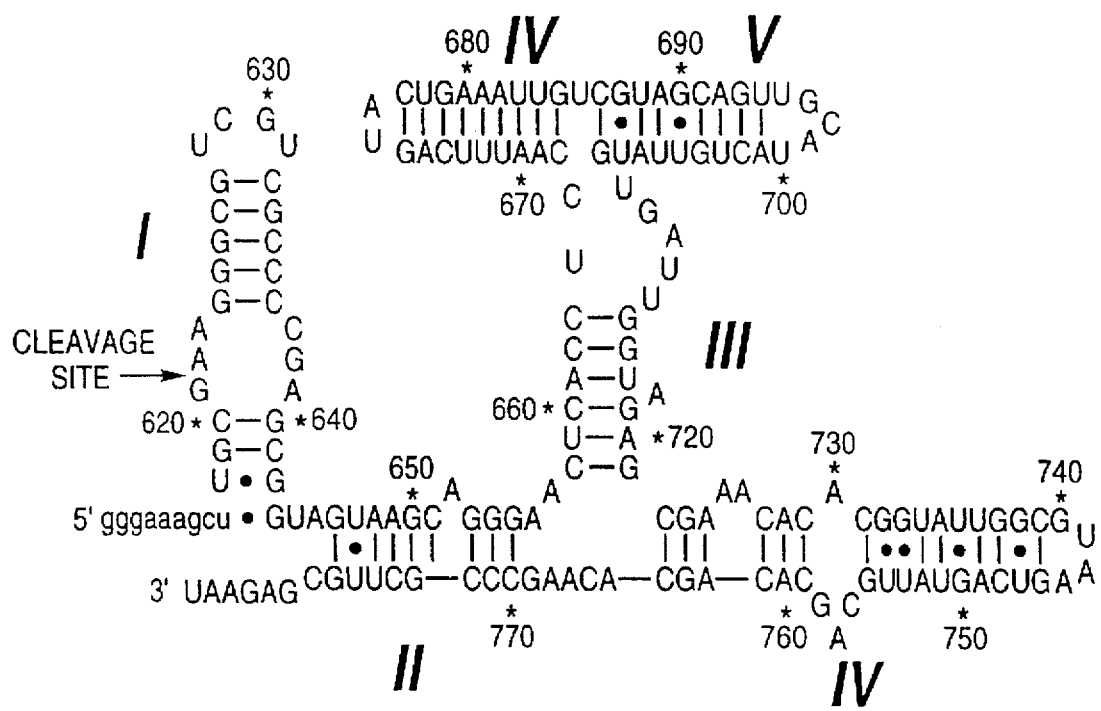
FIG. 5 is a representation of the general structure of the self-cleaving Neurospora VS RNA enzyme motif (SEQ ID NO. 39).

Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

| Seq. ID No. | nt. Base Reference Number | mRNA Target Sites |
|---|---|---|
| bcr | | |
| 01 | 3135 | CUGAUCUCCUCUGACUAUG |
| 02 | 3196 | GUGUUUCAGAAGCUU |
| 03 | 3214 | CCUGACAUCCGUGG |
| 04 | 3226 | GGAGCUGCAGAUGCUGACCA |
| 05 | 3245 | CAACUCGUGUGUGAAACUCC |
| 06 | 3264 | CAGACUGUCCACAGCAUUCCGCUGAC |
| 07 | 3282 | CCGCUGACCAUCAAUAAGG |
| 08 | 3333 | CUGAAUGUCAUCGUCCA |
| 09 | 3360 | GAUUUAAGCAGAGUUCAA |
| abl | | |
| 10 | 445 | AGCCCUUCAGC |
| 11 | 459 | CAGUAGCAUCUG |
| 12 | 488 | CUGAGUGAA |
| 13 | 542 | GAAAAUGACCCC |
| 14 | 554 | AACCUUUCGUUGC |
| 15 | 571 | GUAUGAUUUGUG |
| 16 | 592 | AGAUAACACUCUAAGC |
| 17 | 607 | CAUAACUAAA |
| 18 | 628 | CCGGGUCUUAGGCUAUAAUCAC |
| 19 | 647 | CACAAUGGGGAAUGG |

TABLE III

Human bcr/abl HH Target Sequence

| Sequence ID No. | HH Target Sequence |
|---|---|
| b2-a2 Junction | |
| 20 | UGACCAUCA AUA AGGAAGAAGCC |
| 21 | GAAGAAGCC CUU GAGCGGCCAGU |
| 22 | AAGAAGCCC UUC AGCGGCCAGUA |
| b3-a2 Junction | |
| 23 | UAAGCAGAG UUC AAAAGCCCUUC |
| 24 | UCAAAAGCC CUU CAGCGGCCAGU |
| 25 | CAAAAGCCC UUC AGCGGCCAGUA |

TABLE IV

Human bcr-abl HH Ribozyme Sequences

| Sequence ID No. | HH Ribozyme Sequence |
|---|---|
| 26 | GGCUUCUUCCU CUGAUGAGGCCGAAAGGCCGAA AUUGAUGGUCA |
| 27 | ACUGGCCGCUG CUGAUGAGGCCGAAAGGCCGAA AGGGCUUCUUC |
| 28 | UACUGGCCGCU CUGAUGAGGCCGAAAGGCCGAA AGGGCUUCUU |
| 29 | GAAGGGCUUUU CUGAUGAGGCCGAAAGGCCGAA AACUCUGCUUA |
| 30 | ACUGGCCGCUG CUGAUGAGGCCGAAAGGCCGAA AGGGCUUUUGA |
| 31 | UACUGGCCGCU CUGAUGAGGCCGAAAGGCCGAA AAGGGCUUUUG |

---

I claim:

1. An enzymatic nucleic acid molecule which specifically cleaves mRNA encoded by a bcr/abl gene, and wherein said nucleic acid binds to the bcr portion of said bcr/abl mRNA.

2. An enzymatic nucleic acid molecule which specifically cleaves mRNA encoded by a bcr/abl gene, and wherein said nucleic acid binds to the abl portion of said bcr/abl mRNA.

3. An enzymatic nucleic acid molecule which specifically cleaves mRNA encoded by a bcr/abl gene; wherein said nucleic acid comprises two target binding arms, one of said binding arms is complementary to the bcr portion and second said arm is complementary to the abl portion of said bcr/abl mRNA; and wherein said nucleic acid cleaves said mRNA immediately after sequence HUH, wherein H represents adenosine, uridine, or cytidine, and U represents uridine.

4. The enzymatic nucleic acid molecule of claim 1, wherein said mRNA is identified as any of SEQ ID NOS. 1–9, and wherein said nucleic acid is in a hepatitis delta virus configuration.

5. The enzymatic nucleic acid molecule of any of claims 1, 2, or 3, wherein said nucleic acid molecule is in a hammerhead motif.

6. The enzymatic nucleic acid molecule of any of claims 1, or 2, wherein said nucleic acid molecule is in a hairpin, hepatitis Delta virus, group I intron, Neurospora VS RNA or RNaseP RNA motif.

7. The enzymatic nucleic acid of any of claims 1, 2, or 3, wherein said nucleic acid comprises between 5 and 23 bases complementary to said mRNA.

8. The enzymatic nucleic acid of any of claims 1, 2, or 3, wherein said nucleic acid comprises between 10 and 18 bases complementary to said mRNA.

9. The enzymatic nucleic acid molecule of claim 5, wherein said nucleic acid comprises a sequence defined as any of SEQ ID NOS. 26–31.

10. The enzymatic nucleic acid of any of claims 1, 2, or 3, wherein said bcr/abl gene is formed by a b2-a2 chromosomal translocation.

11. The enzymatic nucleic acid of any of claims 1, 2, or 3, wherein said bcr/abl gene is formed by a b3-a2 chromosomal translocation.

12. The enzymatic nucleic acid molecule of claim 2, wherein said mRNA is defined as any of SEQ ID NOS. 10–19, and wherein said nucleic acid is in a hepatitis delta virus configuration.

13. The enzymatic nucleic acid molecule of claim 1, wherein said mRNA is defined as any of SEQ ID NOS. 1–3, and 5–9, and wherein said nucleic acid is in a hammerhead configuration.

14. The enzymatic nucleic acid molecule of claim 2, wherein said mRNA is defined as any of SEQ ID NOS. 10, 11, and 14–18, and wherein said nucleic acid is in a hammerhead configuration.

15. The enzymatic nucleic acid molecule of claim 3, wherein said mRNA is defined as any of SEQ ID NOS. 20–25, and wherein said nucleic acid is in a hammerhead configuration.

16. The enzymatic nucleic acid molecule of claim 5, wherein said nucleic acid comprises a stem II region, and wherein the length of said stem II is greater than or equal to 2 base pairs.

17. The enzymatic nucleic acid of claim 6, wherein said hairpin comprises a stem IV region, and wherein the length of said stem IV is greater than or equal to 2 base pairs.

18. The enzymatic nucleic acid of any of claims 4, 1, 2, 3 or 12–15, wherein said nucleic acid comprises at least one sugar modification.

19. The enzymatic nucleic acid of any of claims 4, 1, 2, 3 or 12–15, wherein said nucleic acid comprises at least one base modification.

20. The enzymatic nucleic acid of any of claims 4, 1, 2, 3 or 12–15, wherein said nucleic acid comprises at least one phosphate modification.

21. The enzymatic nucleic acid of any of claims 4, 1, 2, 3 or 12–15, wherein said nucleic acid comprises at least two sugar modifications, wherein one said modification is a 2'-O-methyl and the other said modification is a 2'-deoxy-2'-amino.

22. The enzymatic nucleic acid of any of claims 4, 1, 2, 3 or 12–15, wherein said nucleic acid comprises at least two sugar modifications, wherein one said modification is a 2'-O-methyl and the other said modification is a 2'-C-allyl.

23. The enzymatic nucleic acid of claim 20, wherein said phosphate modification is a phosphorothioate.

24. A mammalian cell comprising an enzymatic nucleic acid molecule of any of claims 4, 1, 2, 3 or 12–15.

25. The cell of claim 7, wherein said cell is a human cell.

26. An expression vector including nucleic acid encoding the enzymatic nucleic acid molecule or multiple enzymatic nucleic molecules of any of claims 4, 1, 2, 3 or 12–15 in a manner which allows expression and delivery of that enzymatic nucleic acid molecule within a mammalian cell.

* * * * *

SEQUENCE LISTING ( 1 ) GENERAL INFORMATION:

( i i i ) NUMBER OF SEQUENCES: 39

( 2 ) INFORMATION FOR SEQ ID NO: 1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

CUGAUCUCCU CUGACUAUG 19

( 2 ) INFORMATION FOR SEQ ID NO: 2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

GUGUUUCAGA AGCUU 15

( 2 ) INFORMATION FOR SEQ ID NO: 3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CCUGACAUCC GUGG 14

( 2 ) INFORMATION FOR SEQ ID NO: 4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GGAGCUGCAG AUGCUGACCA 20

( 2 ) INFORMATION FOR SEQ ID NO: 5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

CAACUCGUGU GUGAAACUCC 20

( 2 ) INFORMATION FOR SEQ ID NO: 6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CAGACUGUCC ACAGCAUUCC GCUGAC                26

( 2 ) INFORMATION FOR SEQ ID NO: 7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CCGCUGACCA UCAAUAAGG                19

( 2 ) INFORMATION FOR SEQ ID NO: 8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CUGAAUGUCA UCGUCCA                17

( 2 ) INFORMATION FOR SEQ ID NO: 9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GAUUUAAGCA GAGUUCAA                18

( 2 ) INFORMATION FOR SEQ ID NO: 10:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

AGCCCUUCAG C                11

( 2 ) INFORMATION FOR SEQ ID NO: 11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CAGUAGCAUC UG                12

( 2 ) INFORMATION FOR SEQ ID NO: 12:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

CUGAGUGAA                                                                    9

( 2 ) INFORMATION FOR SEQ ID NO: 13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

GAAAAUGACC CC                                                                12

( 2 ) INFORMATION FOR SEQ ID NO: 14:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

AACCUUUUCG UUGC                                                              14

( 2 ) INFORMATION FOR SEQ ID NO: 15:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

GUAUGAUUUU GUG                                                               13

( 2 ) INFORMATION FOR SEQ ID NO: 16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

AGAUAACACU CUAAGC                                                            16

( 2 ) INFORMATION FOR SEQ ID NO: 17:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

CAUAACUAAA                                                                   10

( 2 ) INFORMATION FOR SEQ ID NO: 18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

CCGGGUCUUA GGCUAUAAUC AC                                                     22

( 2 ) INFORMATION FOR SEQ ID NO: 19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

CACAAUGGGG AAUGG        15

( 2 ) INFORMATION FOR SEQ ID NO: 20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

UGACCAUCAA UAAGGAAGAA GCC        23

( 2 ) INFORMATION FOR SEQ ID NO: 21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 21:

GAAGAAGCCC UUCAGCGGCC AGU        23

( 2 ) INFORMATION FOR SEQ ID NO: 22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 22:

AAGAAGCCCU UCAGCGGCCA GUA        23

( 2 ) INFORMATION FOR SEQ ID NO: 23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 23:

UAAGCAGAGU UCAAAAGCCC UUC        23

( 2 ) INFORMATION FOR SEQ ID NO: 24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:

UCAAAAGCCC UUCAGCGGCC AGU        23

( 2 ) INFORMATION FOR SEQ ID NO: 25:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

CAAAAGCCCU UCAGCGGCCA GUA     23

( 2 ) INFORMATION FOR SEQ ID NO: 26:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 26:

GGCUUCUUCC UCUGAUGAGG CCGAAAGGCC GAAAUUGAUG GUCA     44

( 2 ) INFORMATION FOR SEQ ID NO: 27:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

ACUGGCCGCU GCUGAUGAGG CCGAAAGGCC GAAAGGGCUU CUUC     44

( 2 ) INFORMATION FOR SEQ ID NO: 28:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

UACUGGCCGC UCUGAUGAGG CCGAAAGGCC GAAAAGGGCU UCUU     44

( 2 ) INFORMATION FOR SEQ ID NO: 29:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 29:

GAAGGGCUUU UCUGAUGAGG CCGAAAGGCC GAAACUCUG CUUA     44

( 2 ) INFORMATION FOR SEQ ID NO: 30:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 30:

ACUGGCCGCU GCUGAUGAGG CCGAAAGGCC GAAAGGGCUU UUGA     44

( 2 ) INFORMATION FOR SEQ ID NO: 31:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 31:

UACUGGCCGC UCUGAUGAGG CCGAAAGGCC GAAAAGGGCU UUUG      44

( 2 ) INFORMATION FOR SEQ ID NO: 32:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 32:

AGCAGAGUUC AAAAGCCCU      19

( 2 ) INFORMATION FOR SEQ ID NO: 33:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 33:

GGCCGAAAGG CC      12

( 2 ) INFORMATION FOR SEQ ID NO: 34:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.
    The letter "H" stands for A, U or C.

( x i ) SEQUENCE DESCRIPTION: SEQ ID NO: 34:

NNNNUHNNNN N      11

( 2 ) INFORMATION FOR SEQ ID NO: 35:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.

( x i ) SEQUENCE DESCRIPTION: SEQ ID NO: 35:

NNNNNCUGAN GAGNNNNNNC GAAANNNN      28

( 2 ) INFORMATION FOR SEQ ID NO: 36:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.

The letter "Y" stands for pyrimidine bases.
The letter "H" stands for A, U or C.

( x i ) SEQUENCE DESCRIPTION: SEQ ID NO: 36:

NNN Y NGH Y NN NNNN    14

( 2 ) INFORMATION FOR SEQ ID NO: 37:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.

( x i ) SEQUENCE DESCRIPTION: SEQ ID NO: 37:

NNNNNNNGAA GNNNNNNNNN NAAACANNNN NNNNNNNACA UUACNNNNNN    50

( 2 ) INFORMATION FOR SEQ ID NO: 38:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

UGGCCGGCAU GGUCCCAGCC UCCUCGCUGG CGCCGGCUGG GCAACAUUCC GAGGGACCG    60

UCCCCUCGGU AAUGGCGAAU GGGAC    85

( 2 ) INFORMATION FOR SEQ ID NO: 39:

( i ) SEQUENCE CHARACTERISTICS:
        ( A ) LENGTH: 176 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 39:

GGGAAAGCUU GCGAAGGGCG UCGUCGCCCC GAGCGGUAGU AAGCAGGGAA CUCACCUCCA    60

AUUUCAGUAC UGAAAUUGUC GUAGCAGUUG ACUACUGUUA UGUGAUUGGU AGAGGCUAAG    120

UGACGGUAUU GGCGUAAGUC AGUAUUGCAG CACAGCACAA GCCCGCUUGC GAGAAU    176